(12) United States Patent
Müller

(10) Patent No.: US 6,530,688 B1
(45) Date of Patent: Mar. 11, 2003

(54) ROBOT MANIPULATOR FOR MEDICAL IMAGING MEANS

(75) Inventor: Timo Müller, Espoo (FI)

(73) Assignee: Planmeca Oy, Helsinki (FI)

( * ) Notice: Subject to any disclaimer, the term of this patent is extended or adjusted under 35 U.S.C. 154(b) by 0 days.

(21) Appl. No.: 09/581,416

(22) PCT Filed: Dec. 11, 1998

(86) PCT No.: PCT/FI98/00968

§ 371 (c)(1),
(2), (4) Date: Sep. 8, 2000

(87) PCT Pub. No.: WO99/30614

PCT Pub. Date: Jun. 24, 1999

(30) Foreign Application Priority Data

Dec. 12, 1997 (FI) .................................................. 974503

(51) Int. Cl.⁷ ................................................ H05G 1/02
(52) U.S. Cl. .......................................... 378/197; 378/38
(58) Field of Search .......................... 378/197, 37, 38, 378/39, 40, 167, 189, 193, 208

(56) References Cited

U.S. PATENT DOCUMENTS 5,299,288 A      3/1994   Glassman et al. ............ 395/80
5,425,065 A  *  6/1995   Jarvenin ....................... 378/40
5,813,287 A      9/1998   McMurtry et al.

FOREIGN PATENT DOCUMENTS

EP       0506172      9/1992
GB       2144711      3/1985
JP       57-194372  * 11/1982 .................. 378/17

OTHER PUBLICATIONS

Translation of "57–194372, Nov. 1982, Japan, Takakasu".*

* cited by examiner

*Primary Examiner*—Robert H. Kim
*Assistant Examiner*—Hoon K. Song
(74) *Attorney, Agent, or Firm*—Steinberg & Raskin, P.C.

(57) ABSTRACT

The invention relates to a medical imaging means including a movement mechanism (10). The movement mechanism (10) comprises a first mounting part (21) and a second mounting part (22) and at least three link arm members. The link arm assemblies of the mechanism include actuator means and a link arm member or a set of link arm members. The movement mechanism is used for moving a medical imaging device or a part thereof.

17 Claims, 7 Drawing Sheets

FIG. 8

ROBOT MANIPULATOR FOR MEDICAL IMAGING MEANS

FIELD OF THE INVENTION

The present invention relates to a medical imaging means including a movement mechanism having a first mounting part and a second mounting part and at least three link arm assemblies, said link arm assemblies including actuator means and a link arm member or a set of link arm members, whereby said movement mechanism is used for moving a medical imaging device or a part thereof.

BACKGROUND OF THE INVENTION

A great number of medical imaging methods require the movement of the imaging device or parts thereof. Such a movement can be orbital, rotational or linear. In conventional systems, the implementation of the movements requires extremely complicated arrangements.

The use of parallel-arm mechanisms is known from robotic systems for implementing a 3-dimensional movement. Such an arrangement has two essentially planar elements connected to each other by link arms or pairs of link arms of a controllable length. In the following text, such an arrangement is called a parallel-arm mechanism. One of the planar elements is fastened to a support structure, while the other planar element carries mounted thereon the means whose movement is desired. By adjusting the length of the link arms by active actuator means, a complete 3-dimensional freedom of movement is attained over spatial area needed for a specific task. Such a mechanism is commonly used in, e.g., machining equipment, aircraft simulators and placement of electronic components.

OBJECTS AND SUMMARY OF THE INVENTION

It is an object of the present invention to provide an improved medical imaging means and particularly an improved movement mechanism for use with the same.

It is a particular object of the present invention to provide an improved movement mechanism for use in conjunction with a panoramic radiography apparatus.

It is a still further particular object of the present invention to provide an improved movement mechanism for use in conjunction with a mammography apparatus.

To achieve the above-described goals and others to be mentioned later in the text, the invention is principally characterized in that

- a first mounting part is adapted mountable on a support structure such as a wall, ceiling or support beam,
- medical imaging device or a part thereof,
- link arm members are pivotally connected at pivot points to said first mounting part and said second mounting part,
- the length or position of said link arm members is adapted controllable by an actuator means, and
- the position, inclination and/or rotation of said second mounting part is adapted controllable by virtue of adjusting the length of the link arm members and/or the height of their pivot point.

In the invention, the above-mentioned parallel-arm mechanism has been adapted to a novel application, namely, for implementing the trajectory of dynamically moving members in medical imaging apparatuses. No movement mechanism of a medical imaging apparatus is known in the art to be constructed using this type of parallel arm mechanism.

Medical imaging apparatuses pose extremely tight requirements on the accuracy of an arrangement implementing a trajectory. The use of a parallel-arm mechanism in such demanding applications as machining equipment has proved its capability of accomplishing an extremely precise and smooth trajectory.

The unlimited degree of freedom achievable by a parallel-arm mechanism in 3-dimensional dynamic movements over a desired area facilitates the implementation of all known imaging modes including fluoroscopy, 3D tomography, tomosynthesis imaging and slit fluoroscopy.

The use of a parallel-arm mechanism for implementing the trajectories required in a medical imaging apparatus is particularly advantageous owing to the simple construction of such a movement mechanism. Hence, the structure of the mechanism is more cost-efficient in production than conventional constructions and it is easily connectable to other parts of an imaging apparatus. The accuracy of the trajectory thus accomplished is excellent which is a significant benefit in medical imaging.

BRIEF DESCRIPTION OF THE DRAWINGS

In the following, the invention is described in greater detail with reference to a preferred embodiment thereof having a nonlimiting character to the scope and spirit of the invention, said embodiment being illustrated in the appended drawings in which.

DETAILED DESCRIPTION OF THE INVENTION

Figure 1:
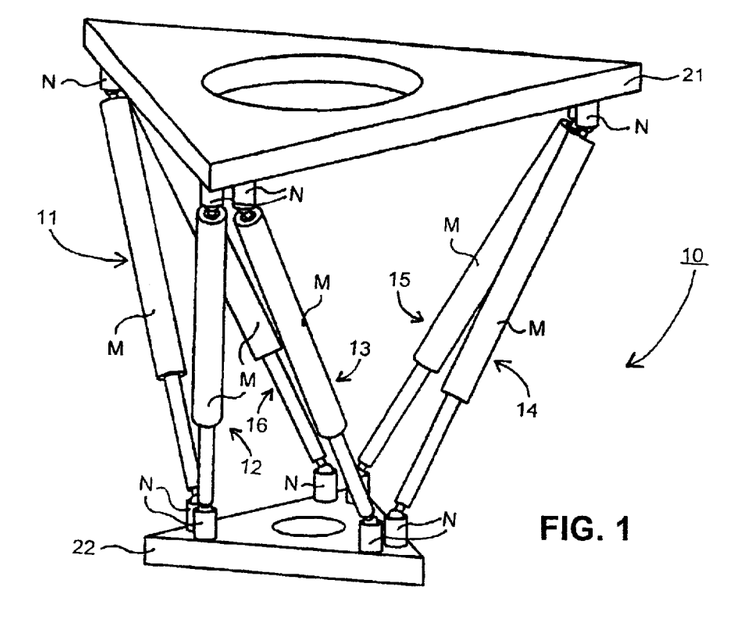
FIG. 1 shows a general view of a parallel-arm mechanism.

Now referring to FIG. 1, therein is shown a parallel-arm mechanism 10 in an upright position. There are mounted six link arm members between its first mounting part 21 and its second mounting part 22. While in the illustrated embodiment, the first mounting part 21 and the second mounting part 22 have a triangular shape of essentially planar structure, also mounting parts of any alternative shape are possible in practice.

In the embodiment shown herein, each corner of each triangular mounting part 21, 22 has two connection points for the link arm members. To each triangular corner of the first mounting part 21, there are connected two link arm members having their other ends connected to separate connection points on the second mounting part 22. Either end of the link arm members 11,12,13,14,15,16 is provided with a ball joint N fixed on the mounting parts 21,22. To each link arm member 11,12,13,14,15,16 is adapted an actuator M capable of controlling the length of its dedicated link arm member. By controlling the lengths of the link arm members individually, it is possible to implement a linear, rotational or tilting movement or a combination of these. The lengths of the link arm members are steered according to a predetermined control program.

Figure 2:
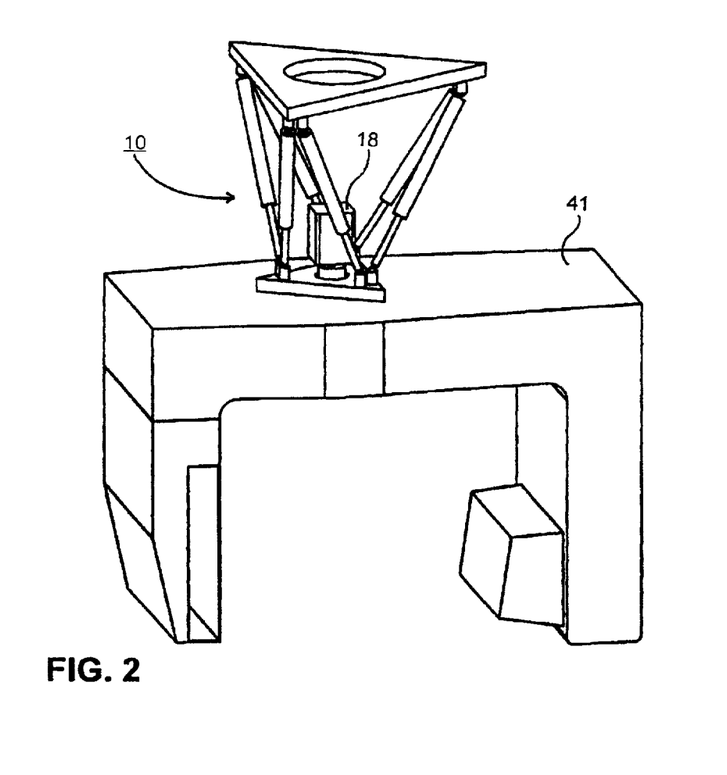
FIG. 2 shows a parallel-arm mechanism connected to the C-arcuate body part used in a panoramic radiography apparatus.

In FIG. 2 is shown a parallel-arm mechanism 10 having its one mounting part carrying a body part 41 shaped as a C-arm. In this embodiment, the C-arm 41 is used in panoramic radiography for the imaging of the jaw bone and the teeth. For this application, the height position of the C-arm 41 and its position in the horizontal plane are controlled. The actual rotating movement required in panoramic radiography is accomplished with the help of an active actuator 18. The actuator M and the active actuator means 18 connected to the link arm members of the parallel-arm mechanism 10 are controlled by a microprocessor-based control system or, using any other type of predetermined control program.

Figure 3A:
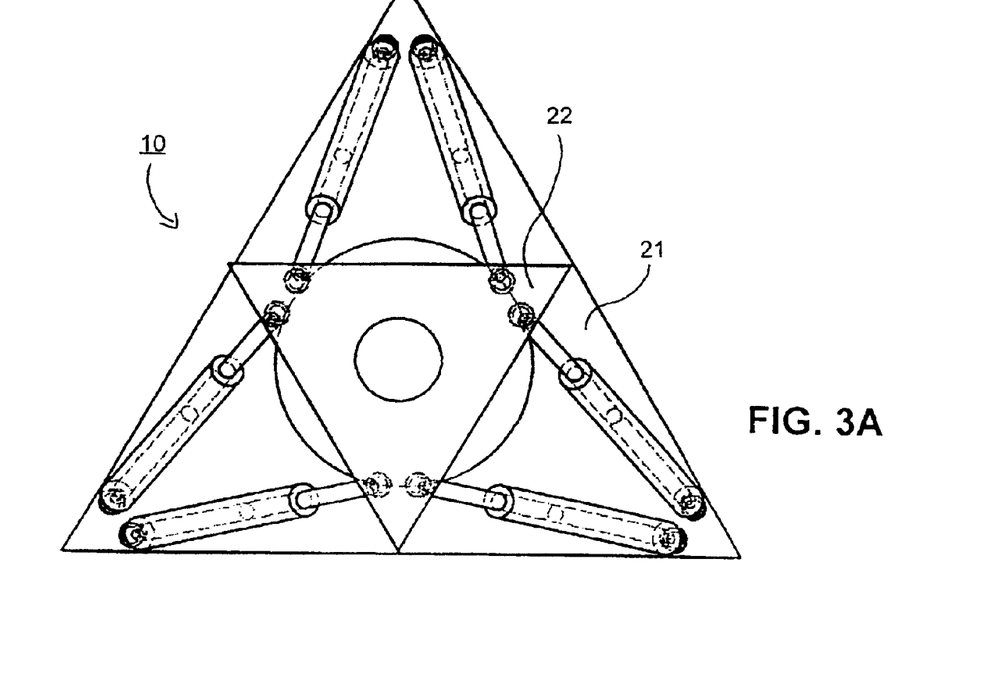
FIG. 3A shows the parallel-arm mechanism from below in its basic position.

In FIG. 3A is shown the parallel-arm mechanism as seen from below in its basic position. In this position, all the link arm members are controlled equally long. The first mounting part 21 and the second mounting part 22 are then parallel and their center points fall on the same axis.

Figure 3B:
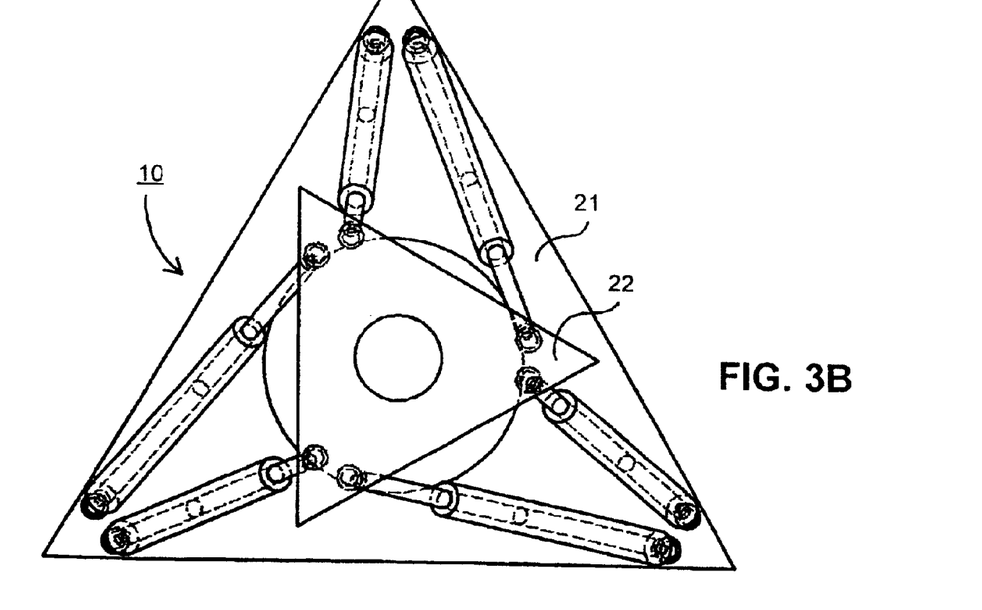
FIG. 3B shows the parallel-arm mechanism from below with its second mounting parts rotated.

In FIG. 3B is shown the parallel-arm mechanism as seen from below with its second mounting part 22 rotated with respect to the basic position (cf. FIG. 3A). The rotational movement is implemented by controlling the lengths of the link arm members.

Figure 3C:
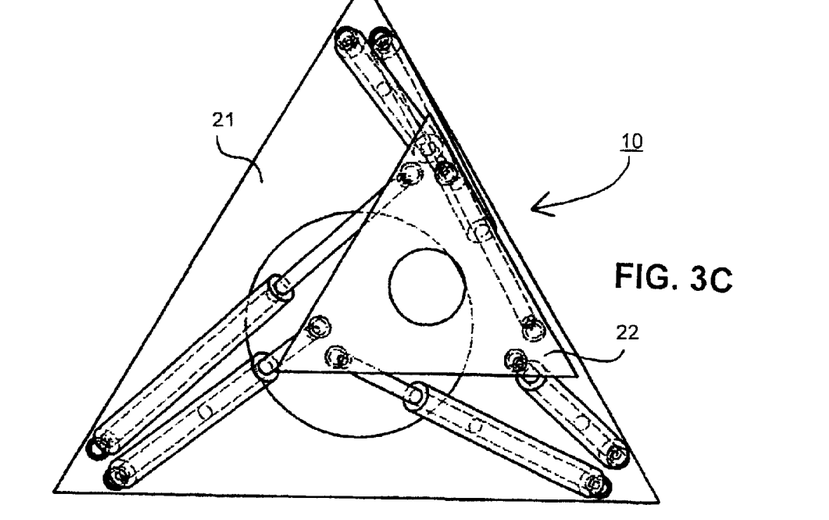
FIG. 3C shows the parallel-arm mechanism from below with its second mounting part rotated and moved.

In FIG. 3C is shown the parallel-arm mechanism as seen from below with its second mounting part 22 rotated and moved away from the center axis of the first mounting part 21.

Figure 3D:
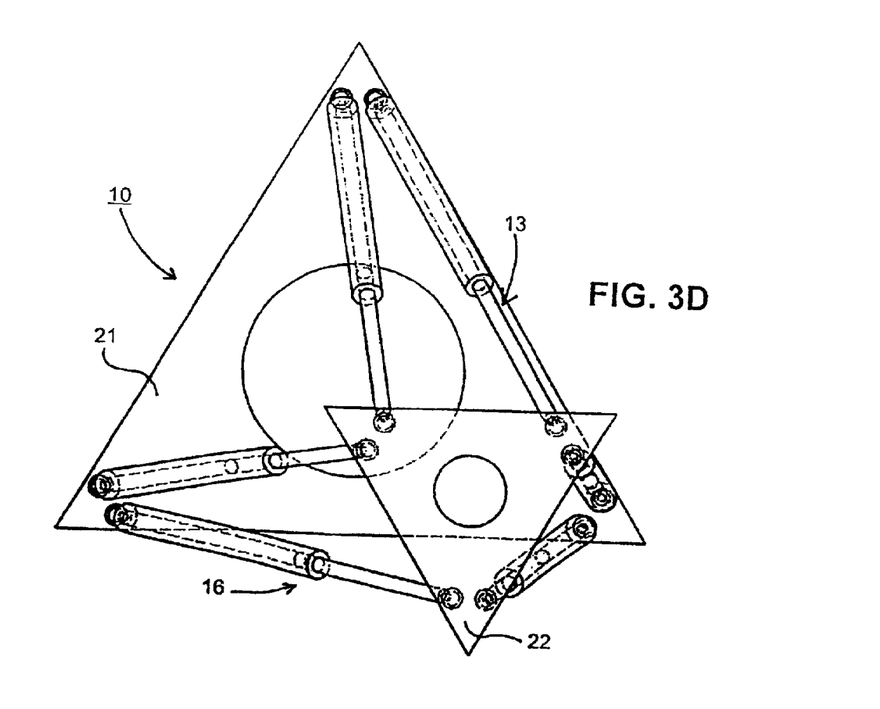
FIG. 3D shows the parallel-arm mechanism from below with its second mounting part moved into its first limit position.
Figure 3E:
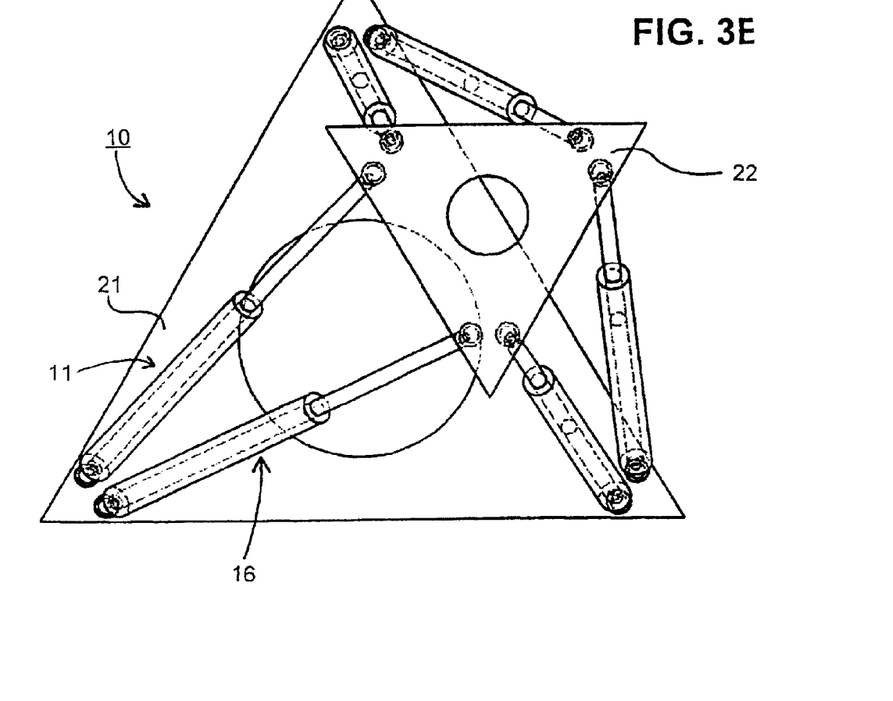
FIG. 3E shows the parallel-arm mechanism from below with its second mounting part moved into its second limit position.

In FIG. 3D is shown the parallel-arm mechanism as seen from below with its second mounting part 22 moved into its first limit position. The link arm members 13 and 16 are controlled into their longest position. From this position, the center point of the second mounting part 22 cannot be moved farther away from the center point of the first mounting part 21, but however the second mounting part 22 can still be rotated or inclined from said position by controlling the lengths of the link arm members In FIG. 3E is shown the parallel-arm mechanism as seen from below with its second mounting part 22 moved into its second limit position. Now the link arm members 11 and 16 are controlled into their longest positions.

Figure 4A:
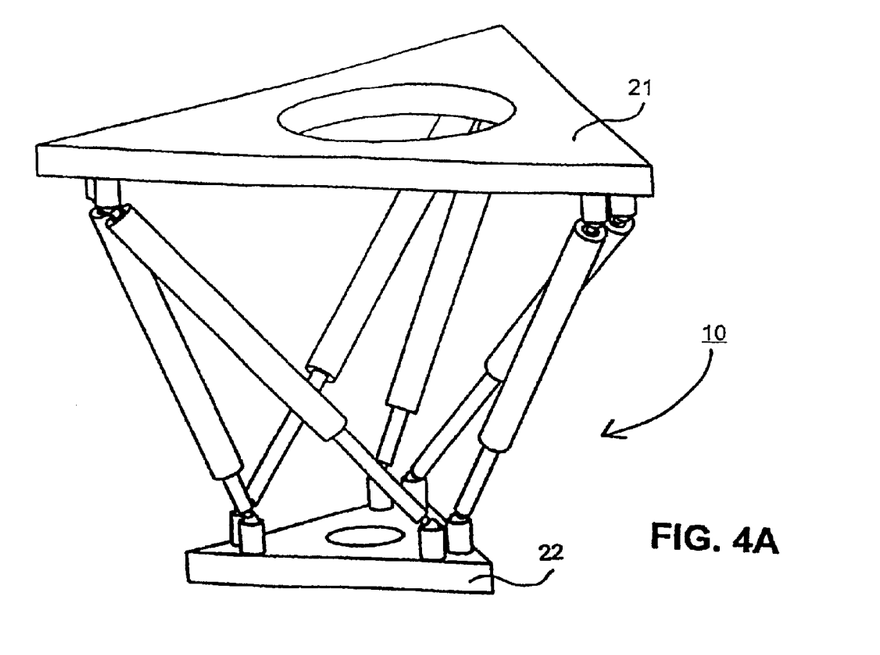
FIG. 4A shows the parallel-arm mechanism in a side view illustrating the situation of FIG. 3C.

In FIG. 4A is shown the situation of FIG. 3C in a side view. In this position, the first mounting part 21 and the second mounting part 22 are situated parallel to each other.

Figure 4B:
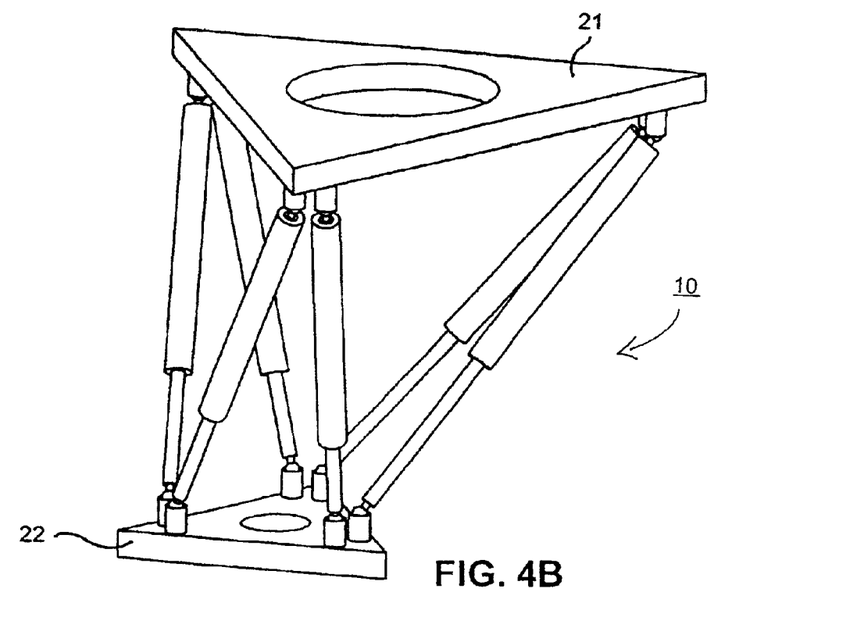
FIG. 4B shows the parallel-arm mechanism in a side view illustrating the situation of FIG. 3E.

In FIG. 4B is shown the situation of FIG. 3E in a side view.

Figure 5:
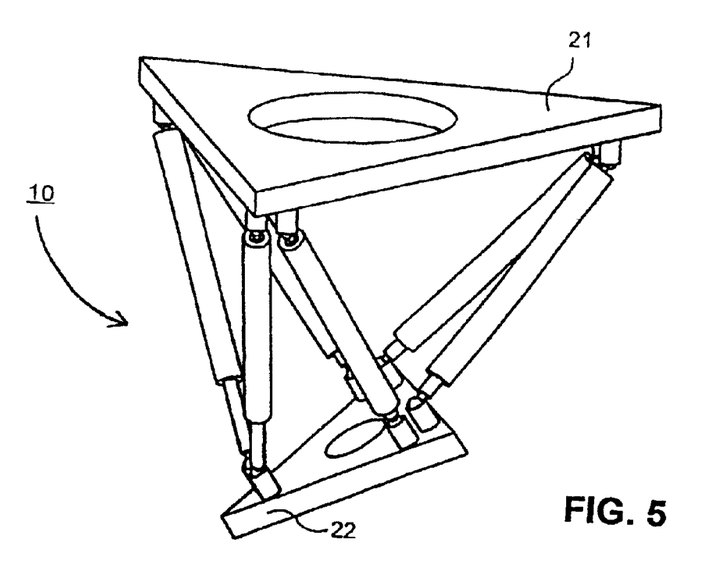
FIG. 5 shows the parallel-arm mechanism in a situation having one of its mounting parts inclined.

In FIG. 5 is shown the parallel-arm mechanism 10 in a position having the second mounting part 22 controlled into an inclined position.

Figure 6:
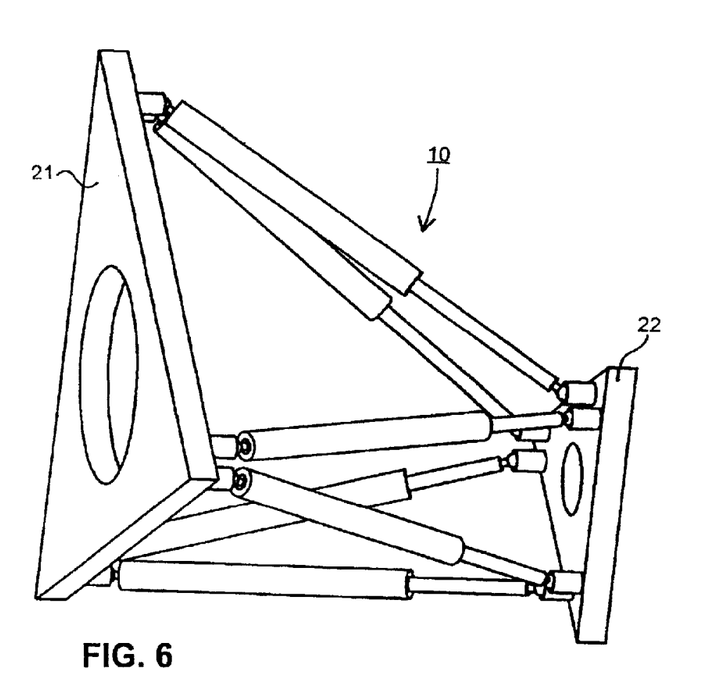
FIG. 6 shows a side mounting of the parallel-arm mechanism.

In FIG. 6 is shown a side mounting of the parallel-arm mechanism 10. Herein, the first mounting part 21 is now oriented upright thus permitting its fastening on, e.g., a wall, support beam or a part of a medical imaging apparatus. The movable part of the imaging apparatus is mounted on the second mounting part 22.

Figure 7:
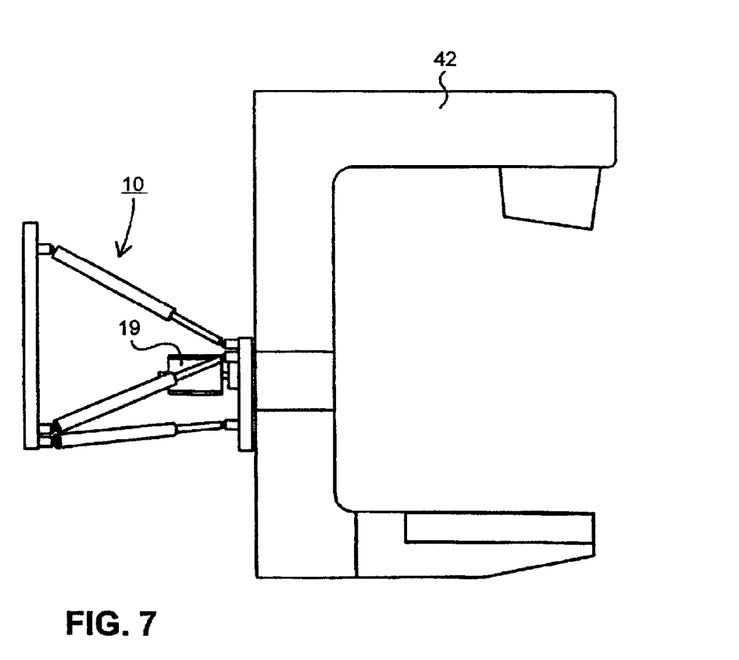
FIG. 7 shows a side mounting of the parallel-arm mechanism; now connected to a C-arcuate body part suited for use in a mammography application.

In FIG. 7 is shown a side mounting of the parallel-arm mechanism, now connected to a C-arcuate body part 42 which in this embodiment is suited for use in a mammography application. This kind of movement mechanism according to the invention offers a greater number of degrees of freedom than conventional constructions of mammography equipment. To the C-arcuate body part 42 of a mammography apparatus is connected an active actuator means 19 in order to provide a rotating movement. The actuators M and the active actuator means 19 that are connected to the fink arm members of the parallel arm mechanism 10 are controlled by a microprocessor-based control system or using any other type of predetermined control program.

Figure 8:
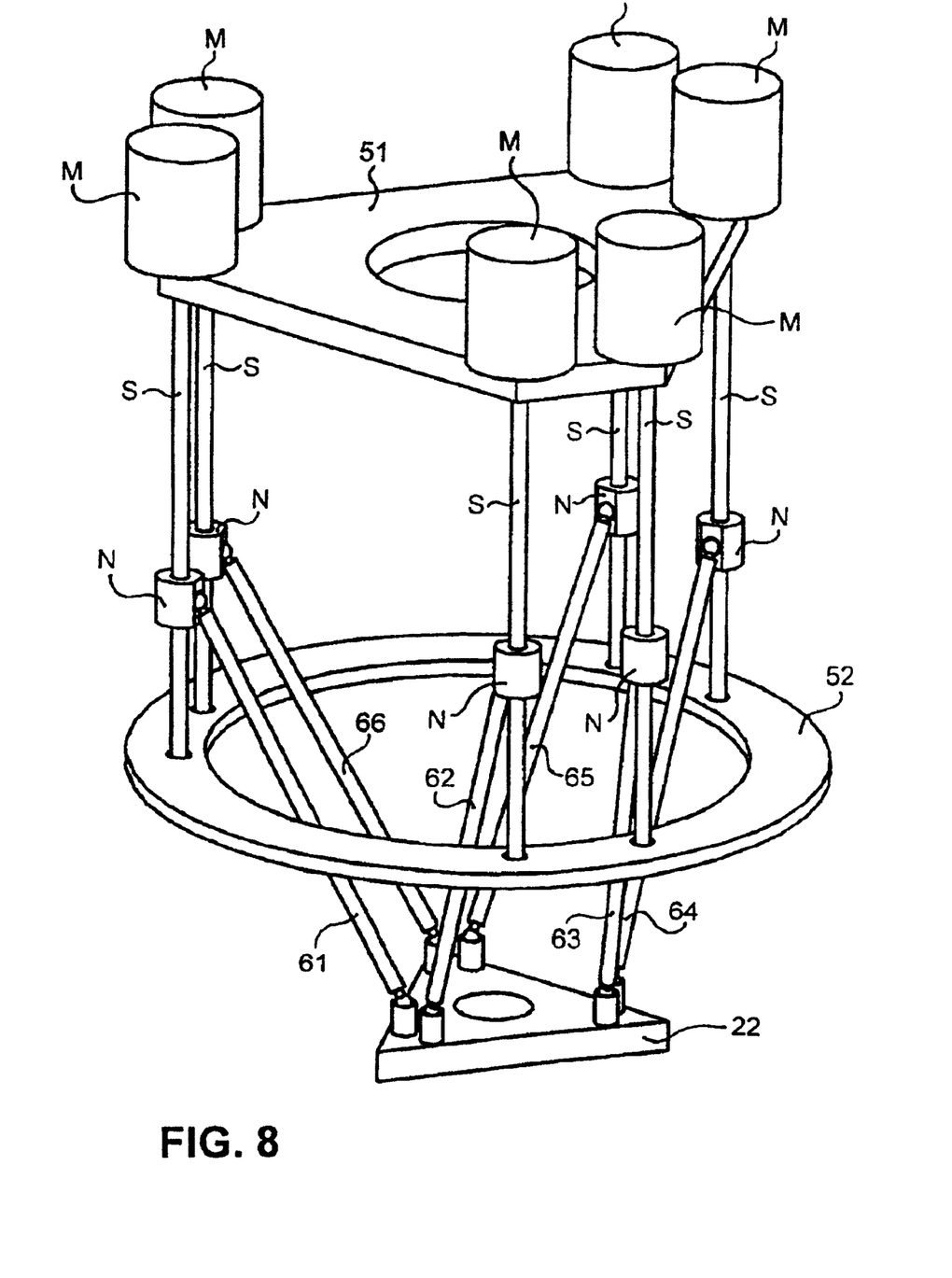
FIG. 8 shows an alternative mechanism for implementing a parallel-arm mechanism.

In FIG. 8 is shown an alternative mechanism for implementing a parallel-arm mechanism. Herein, the first mounting part comprises an upper support plate 51 with actuator motors M and a support ring 52 connected thereto, and threaded control link arms S connecting said support ring 52 to said upper support plate 51. Actuator driven nuts N are adapted to run on the threaded control link arms S. Between the actuator nuts N and the second mounting part 22, there are disposed stiff link arm members 61,62,63,64,65,66, each of which having their first end pivotally connected to the actuator nut N running on the threaded control link arm S and their other end similarly pivotally connected to said second mounting part 22. Each actuator motor M is adapted to rotate the threaded control link arm S connected to the motor output. With the rotation of the threaded control link arm S, the position of the nut N running on the arm.can be changed thus imparting a linear motion on the link arm member 61,62,63,64,65 or 66 which is respectively connected to the nut. Thus, the controlled movement of the connection points of the link arm members on the first mounting part implements the controlled steering of the position, rotation and inclination of the second mounting part 22. The actuators M are controlled by a microprocessor-based control system or using any other type of predetermined control program.

In FIGS. 1–8 are shown the positions of the parallel-arm mechanism members in different stationary positions. Typically, a parallel-arm mechanism is used to accomplish a continuous dynamic movement, and the purpose of the above-described examples is to elucidate the instantaneous positions of the parallel-arm mechanism during its dynamic movement.

According to the needs of any specific application, the above-described movement mechanism may be modified in a plurality of different fashions within the scope and spirit of the invention. For instance, the first mounting part 21 and the second mounting part 22 may be designed into the shape of any feasible and practicable structure. The first mounting part 21 of the parallel-arm mechanism may alternatively be fastened to the ceiling of the radiography room or to a separate support beam or other part of the imaging apparatus.

The scope of the invention is defined in the appended claims.

What is claimed is:

1. Medical imaging means comprising a movement mechanism having a first mounting part (21) and a second mounting part (22) and at least three link arm assemblies (12, 14, 16) that include actuator means (M) and a link arm member or a set of link arm members, said movement mechanism being used for moving a medical imaging device or a part thereof, wherein said first mounting part (21) is mounted on a support structure, said second mounting part (22) is coupled to a medical imaging device or a part thereof, said link arm members are pivotally connected at pivot points to said first mounting part (21) and said second mounting part (22), the length or position of said link arm members being controllable by an actuator means (M), the position, inclination and/or rotation of said second mounting part (22) being controllable by virtue of adjusting the length of the link arm members and/or the height of their pivot points and an active actuator means (18) is operably coupled to the imaging means of the medical imaging device that rotates the imaging means.

2. Imaging means according to claim 1, wherein the trajectory of said second mounting part (22) is steered by a control system based on a microprocessor and a computer program.

3. Imaging means according to claim 1, wherein said actuator means (M) is a hydraulic cylinder.

4. Imaging means according to claim 1, wherein said actuator means (M) is a linear motor.

5. Imaging means according to claim 1, wherein to said second mounting part (22) are coupled means required for imaging with the help of a medical imaging device.

6. Imaging means according to claim 1, wherein to said second mounting part (22) is coupled a C-arcuate body part (41) of a panoramic imaging apparatus having one end of the arcuate body part carrying a source of radiation and the other end carrying a detector of said radiation.

7. Imaging means according to claim 6, wherein said active actuator means (18) is capable of rotating said C-arcuate part (41) of said panoramic imaging apparatus.

8. Imaging means according to claim 1, wherein to said second mounting part (22) is coupled a C-arcuate body part (42) of a mammography apparatus.

9. Imaging means according to claim 8, wherein to said second mounting part (22) is coupled an active actuator means (19) capable of rotating said C-arcuate body part (42) of said mammography apparatus.

10. A medical imaging assembly comprising:

a first mounting part adapted for attachment to a support structure;

a second mounting part adapted for attachment to a medical imaging device;

at least three link arm assemblies structured and arranged for interconnecting said first and second mounting parts, each link arm assembly including a link arm having an adjustable length, each of said link arms being attached at a first end to said first mounting part by a universal joint connection and at a second end to said second mounting part by another universal joint connection, means for selectively controlling the length of said link arm; and an actuator operably coupled to said medical imaging device for rotating said medical imaging device.

11. The medical imaging assembly according to claim 10, wherein the lengths of said link arms are adjusted according to a control system including a microprocessor and a computer program.

12. The medical imaging assembly according to claim 10, wherein said means for selectively controlling the length of said arm comprises a hydraulic cylinder.

13. The medical imaging assembly according to claim 10, wherein said means for selectively controlling the length of said arm comprises a linear motor.

14. The medical imaging assembly according to claim 10, further comprising an arcuate body part of a panoramic imaging apparatus coupled to said second mounting part, said arcuate body part having a first end including a source of radiation and a second end having a detector for detecting radiation.

15. The medical imaging assembly according to claim 14, wherein said actuator coupled to said medical imaging device is operably coupled to said arcuate body part of said panoramic imaging apparatus.

16. The medical imaging assembly according to claim 10, further comprising an arcuate body part of a mammography apparatus coupled to said second mounting part.

17. The medical imaging assembly according to claim 16, wherein said actuator coupled to said medical imaging device is operably coupled to said arcuate body of said mammography apparatus.

* * * * *